United States Patent
Schoendube et al.

(10) Patent No.: US 11,568,585 B2
(45) Date of Patent: Jan. 31, 2023

(54) METHOD FOR THE ARTIFACT CORRECTION OF THREE-DIMENSIONAL VOLUME IMAGE DATA

(71) Applicant: Siemens Healthcare GmbH, Erlangen (DE)

(72) Inventors: Harald Schoendube, Erlangen (DE); Johan Sunnegaardh, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 363 days.

(21) Appl. No.: 16/710,775

(22) Filed: Dec. 11, 2019

(65) Prior Publication Data
US 2020/0193656 A1 Jun. 18, 2020

(30) Foreign Application Priority Data
Dec. 17, 2018 (DE) .......................... 102018221943.5

(51) Int. Cl.
*G06T 11/00* (2006.01)
*G06N 3/08* (2006.01)
(Continued)

(52) U.S. Cl.
CPC ............ *G06T 11/008* (2013.01); *A61B 6/032* (2013.01); *A61B 6/4078* (2013.01);
(Continued)

(58) Field of Classification Search
CPC ........... A61B 6/00; A61B 6/03; A61B 6/4085; A61B 6/4078; A61B 6/032; A61B 6/5258;
(Continued)

(56) References Cited

U.S. PATENT DOCUMENTS

| 2012/0183194 A1* | 7/2012 | Brown | G06T 11/008 |
| | | | 382/131 |
| 2016/0242740 A1* | 8/2016 | Day | A61B 8/14 |
| 2019/0073804 A1 | 3/2019 | Allmendinger | |

FOREIGN PATENT DOCUMENTS

| EP | 3451284 A1 | 3/2019 |
| WO | WO 2011042821 A1 | 4/2011 |

OTHER PUBLICATIONS

Brown, Kevin M. et al. "Method for Reducing Windmill Artifacts in Multi-Slice CT Images" Proceedings vol. 7961, Medical Imaging 2011: Physics of Medical Imaging; 79611P (2011) // (Philips Healthcare)—https://doi.org/10.1117/12.877437.

* cited by examiner

*Primary Examiner* — Tuan H Nguyen
(74) *Attorney, Agent, or Firm* — Harness, Dickey & Pierce, P.L.C.

(57) ABSTRACT

A method for the artifact correction of three-dimensional volume image data of an object is disclosed. In an embodiment, the method includes receiving first volume image data via a first interface, the first volume image data being based on projection measurement data acquired via a computed tomography device, the computed tomography device including a system axis, and the first volume image data including an artifact including high-frequency first portions in a direction of a system axis and including second portions, being low-frequency relative to the high-frequency first portions, in a plane perpendicular to the system axis; ascertaining, via a computing unit, artifact-corrected second volume image data by applying a trained function to the first volume image data received; and outputting the artifact-corrected second volume image data via a second interface.

22 Claims, 4 Drawing Sheets

(51) Int. Cl.
*G06N 20/00* (2019.01)
*A61B 6/00* (2006.01)
*A61B 6/03* (2006.01)

(52) U.S. Cl.
CPC .......... *A61B 6/4085* (2013.01); *A61B 6/5258* (2013.01); *G06N 3/08* (2013.01); *G06N 20/00* (2019.01); *G06T 2210/41* (2013.01); *G06T 2211/424* (2013.01)

(58) Field of Classification Search
CPC ... G06T 11/00; G06T 11/008; G06T 2210/41; G06T 2211/424; G06N 20/00; G06N 3/08
See application file for complete search history.

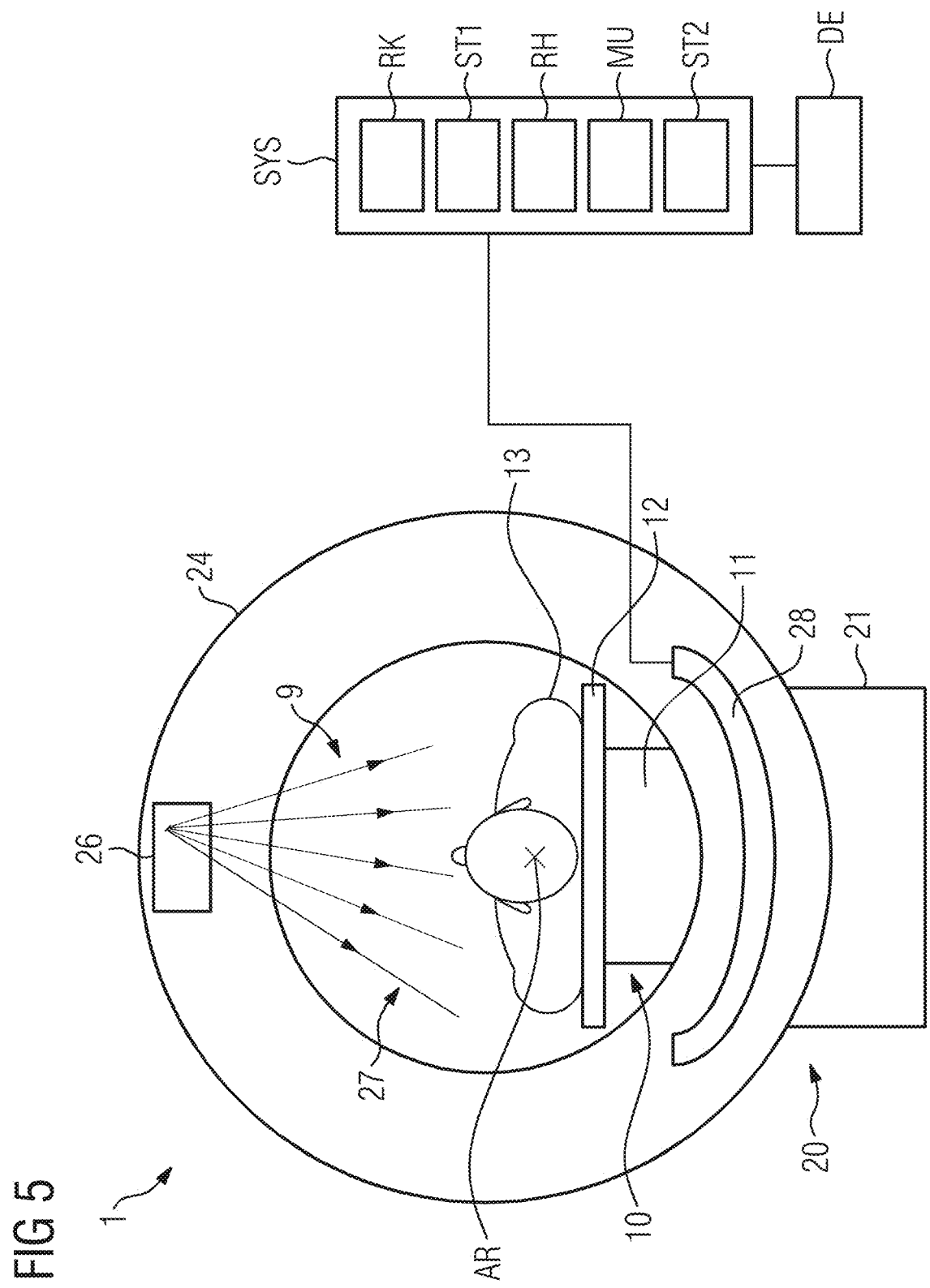

METHOD FOR THE ARTIFACT CORRECTION OF THREE-DIMENSIONAL VOLUME IMAGE DATA

PRIORITY STATEMENT

The present application hereby claims priority under 35 U.S.C. § 119 to German patent application number DE 102018221943.5 filed Dec. 17, 2018, the entire contents of which are hereby incorporated herein by reference.

FIELD

Embodiments of the invention generally relate to a method for the artifact correction of three-dimensional volume image data; a correction system for the artifact correction of three-dimensional volume image data; as well as a computed tomography device which in particular comprises such a correction system. Furthermore, embodiments of the invention generally relate to a method for the adjustment of a trained function, a training system for the adjustment of such a trained function, as well as a computer program product and a computer-readable storage medium.

BACKGROUND

Computed tomography (CT) is an imaging method which is used primarily for medical diagnosis. In computed tomography, for the acquisition of spatially three-dimensional volume image data, an X-ray tube, as well as an X-ray detector interacting with said X-ray tube, rotate around an object to be examined. For this purpose, in a computed tomography device (CT device), the X-ray tube and the X-ray detector are arranged on a rotating assembly or rotor, which during operation of the CT device performs a rotational movement around an axis, along which the object to be mapped is positioned. This axis is generally also referred to by the person skilled in the art as a system axis or as the z axis of the CT device. Nowadays, spiral and/or multi-slice CT devices are used in this context in medical imaging as a rule. In a spiral CT, the object experiences a continuous feed through the CT device, while X-ray tube and X-ray detector steadily rotate around the object. The X-ray beam of the X-ray tube thus describes a continuous spiral around the object. The term multi-slice or multi-row CT refers to the X-ray detector used, which does not only comprise one row or line of detector elements, but rather a plurality of rows or lines lying adjacent to one another in the direction of the system axis, meaning that a plurality of slices of the object are simultaneously acquired for each orbit of the X-ray tube.

During the rotational movement of the X-ray tube, projection measurement data is acquired via the X-ray detector for a plurality of angular directions. The projection measurement data involves a projection or a plurality of projections, which contain information regarding the attenuation of the radiation through the examination object for the respective angular direction. The projection measurement data is also referred to as raw data or as a raw data set. From this projection measurement data, it is subsequently possible for two-dimensional sectional image data or three-dimensional volume image data of the examination object to be reconstructed or calculated, for example by way of what is known as a filtered back projection method (FBP).

One prominent example of an artifact in CT imaging is what is known as the "windmill artifact". In particular, such a windmill artifact is characterized by high-frequency portions in the volume image data in the direction of the system axis and portions in the image plane perpendicular to the system axis which are low-frequency in relation thereto.

The windmill artifact occurs as part of multi-slice spiral CT imaging and results from the sub-sampling by the specified detector elements in the z direction which is intrinsically inherent with the X-ray detector and thus from the non-fulfillment of the Shannon sampling theorem along the system axis. In this context, a windmill artifact occurs in particular in connection with high-contrast jumps along the system axis, i.e. in the presence of a strong gradient in the X-ray contrast in the object to be acquired in the direction of the system axis. This may be caused by adjacent materials in the object with strongly differing absorption behavior for X-ray radiation, such as in the region of the vertebral body of the spinal column of a patient.

Solution approaches lie in the reconstruction of thicker slices, for example, wherein by way of the suitable combination of detector rows lying adjacent to one another in the direction of the system axis, the sampling theorem can be fulfilled. This, however, is associated with a loss in image resolution in the direction of the system axis. Furthermore, a CT device with what is known as a "spring focus" in the direction of the system axis can be used. In this context, every second acquisition of a raw data set is shifted in the direction of the system axis by the width of half a detector row, and thus the sampling theorem is approximately fulfilled. The disadvantage of this is in particular the very high structural outlay. Furthermore, measures may be used which work on the basis of the already-reconstructed image data and, for example, remove or reduce the artifacts from the volume image data by non-linear filters. In this context, an optimum adjustment of the filter parameters is important for an effective and error-free correction of the image data. The disadvantage is that other structures in the object, which have a similar signature, are likewise filtered and thus image information is lost. One example of such a filter method is known from the publication WO 2011/042821 A1 or from "Method for Reducing Windmill Artifacts in Multi-Slice CT" by K. M. Brown et al. (Proc. of SPIE, vol. 7961, 79611P, https://doi.org/10.1117/12.877437).

One further prominent example of an artifact is what is known as a "cone beam artifact". When using a cone beam of the X-ray tube for the exposure of a multi-slice X-ray detector, the slice planes are inclined. The larger the number of detector slices or detector rows, the greater the inclination of the slice planes of the projection measurement data in the edge regions. By way of mathematical simplifications introduced into the reconstruction, this may lead to a cone beam artifact, which likewise has higher-frequency portions in the image data in the direction of the system axis and portions in the plane of the image data perpendicular to the system axis which are low-frequency in relation thereto.

SUMMARY

The inventors note that the cited artifacts can be avoided by way of an iterative reconstruction method. The inventors have discovered that the iterative methods, however, require a considerably higher amount of computational effort with a corresponding computing time compared to filter-based reconstruction methods.

At least one embodiment provides an improved option for correcting an artifact in three-dimensional volume image data, wherein the artifact has high-frequency first portions in the volume image data, in particular in the direction of the system axis of the computed tomography device used for the acquisition, and, in a plane perpendicular to the system axis, has second portions which are low-frequency in relation to the high-frequency first portions.

Embodiments and developments of the invention which are advantageous and in part per se inventive are presented in the subclaims and the description which follows. The methods may in particular involve computer-implemented methods.

An inventive achievement of the embodiments is described below, both in relation to the claimed apparatuses and also in relation to the claimed method. Features, advantages or alternative embodiments mentioned herein are also transferable similarly to the other claimed subject matter and vice versa. In other words, the objective claims (which focus on an apparatus for example) can also be further developed with the features described or claimed in relation to a method. The corresponding functional features of the method are thereby provided by corresponding physical modules.

Furthermore, an inventive achievement of embodiments is described both in relation to methods and apparatuses for the artifact correction of three-dimensional volume image data of an object as well as in relation to methods and apparatuses for the adjustment of a trained function. In this context, features and alternative embodiments of data structures and/or functions in methods and apparatuses for the artifact correction can be transferred to analogous data structures and/or functions in methods and apparatuses for the adjustment. Analogous data structures may in particular be characterized by the use of the prefix "training". Furthermore, the trained function used in methods and apparatuses for the artifact correction can in particular have been adjusted and/or provided by methods and apparatuses for the adjustment of the trained function.

At least one embodiment of the invention relates to a method for the artifact correction of three-dimensional volume image data of an object, comprising the steps of receiving, ascertaining and outputting. In this context, in the step of receiving, first volume image data is received via a first interface, wherein the first volume image data is based on projection measurement data acquired via a computed tomography device, wherein the computed tomography device has a system axis, and wherein the first volume image data has an artifact which has high-frequency first portions in the direction of the system axis and, in a plane perpendicular to the system axis, has second portions which are low-frequency in relation to the high-frequency first portions. In the step of ascertaining, artifact-corrected second volume image data is ascertained by applying a trained function to the first volume image data via a computing unit. In the step of outputting, the artifact-corrected second volume image data is output via a second interface.

At least one embodiment of the invention additionally relates to a method for the adjustment of a trained function comprising the steps of the first receiving, the second receiving and the ascertaining, as well as the third receiving and the adjusting. In this context, in the step of the first receiving, the trained function is received via a training interface. In the step of the second receiving via the training interface, artifact-affected first volume image data of a training object is received. Here, the first training volume image data has a training artifact, wherein the training artifact has high-frequency first portions in the direction of a first axis and, in a plane perpendicular to the first axis, has second portions which are low-frequency in relation to the high-frequency first portions. In the step of the third receiving, substantially artifact-free second training volume image data of the training object is received via the training interface, wherein the second training volume image data is brought into association with the first training volume image data. In the step of ascertaining, artifact-corrected third training volume image data is ascertained by applying the trained function to the first training volume image data via a training computing unit. In the step of adjusting, the trained function is adjusted on the basis of a comparison of the second training volume image data and the third training volume image data via a training computing unit.

At least one embodiment of the invention furthermore relates to a correction system for the artifact correction of three-dimensional volume image data of an object comprising a first interface embodied for receiving first three-dimensional volume image data, wherein the first volume image data is based on projection measurement data acquired via a computed tomography device, wherein the computed tomography device has a system axis, and wherein the first volume image data has an artifact which has high-frequency first portions in the direction of the system axis and, in a plane perpendicular to the system axis, has second portions which are low-frequency in relation to the high-frequency first portions. The correction system additionally comprises a computing unit, embodied for ascertaining artifact-corrected second volume image data by applying a function trained via a machine learning method to the first volume image data. Furthermore, the correction system comprises a second interface embodied for outputting the artifact-corrected second volume image data.

Such a correction system may be embodied, in particular, to carry out the method according to at least one embodiment of the invention described above and its aspects. The correction system may be embodied to carry out this method and its aspects in that the interfaces and the computing unit are embodied to carry out the corresponding method steps.

At least one embodiment of the invention additionally relates to a computed tomography device, which is embodied to acquire projection measurement data of an object and which additionally comprises a correction system according to an embodiment of the invention as has been described above.

Moreover, at least one embodiment of the invention relates to a training system for the adjustment of a trained function comprising a training interface embodied for the first receiving of the trained function, furthermore embodied for the second receiving of artifact-affected first training volume image data of a training object having a training artifact, wherein the training artifact has high-frequency first portions in the direction of a first axis and, in a plane perpendicular to the first axis, has second portions which are low-frequency in relation to the high-frequency first portions, furthermore embodied for the third receiving of substantially artifact-free third training volume image data of the training object. The training system additionally has a training computing unit, embodied for ascertaining artifact-corrected second training volume image data by applying the trained function to the first training volume image data, and furthermore embodied for adjusting the trained function on the basis of a comparison of the second training volume image data and the third training volume image data.

Such a training system may be embodied, in particular, to carry out the method according to the invention described above for adjusting a trained function, and its aspects. The training system is embodied to carry out this method and its aspects in that the interface and the computing unit are embodied to carry out the corresponding method steps.

At least one embodiment of the invention also relates to computer program products with computer programs as well as computer-readable media.

In particular, at least one embodiment of the invention relates to a computer program product with a computer program, which is able to be loaded directly into a memory of a correction system and/or of a training system, with program sections in order to carry out all steps of the method for the artifact correction of at least one embodiment and/or in order to carry out all steps of the method for the adjustment of a trained function of at least one embodiment, when the program sections are executed by the correction system and/or the training system.

At least one embodiment of the invention also relates to a method for artifact correction of three-dimensional volume image data of an object, comprising:

receiving first volume image data via a first interface, the first volume image data being based on projection measurement data acquired via a computed tomography device, the computed tomography device including a system axis, and the first volume image data including an artifact including high-frequency first portions in a direction of a system axis and including second portions, being low-frequency relative to the high-frequency first portions, in a plane perpendicular to the system axis, has;

ascertaining, via a computing unit, artifact-corrected second volume image data by applying a trained function to the first volume image data received; and outputting the artifact-corrected second volume image data via a second interface.

At least one embodiment of the invention also relates to a method for adjustment of a trained function, comprising:

first receiving the trained function via a training interface;

second receiving, via the training interface, artifact-affected first training volume image data of a training object, including a training artifact, the training artifact including high-frequency first portions in a direction of a first axis and, in a plane perpendicular to the first axis, including second portions which are low-frequency relative to the high-frequency first portions;

third receiving, via the training interface, substantially artifact-free second training volume image data of the training object, the second training volume image data being brought into association;

ascertaining artifact-corrected third training volume image data by applying the trained function to the first training volume image data via a training computing unit; and adjusting the trained function based upon a comparison of the second training volume image data and the third training volume image data via a training computing unit.

At least one embodiment of the invention also relates to a correction system for artifact correction of three-dimensional volume image data of an object, comprising:

a first interface, to receive first three-dimensional volume image data, the first volume image data being based on projection measurement data acquired via a computed tomography device, the computed tomography device including a system axis and the first volume image data including an artifact including high-frequency first portions in a direction of the system axis and, in a plane perpendicular to the system axis, including second portions which are low-frequency relative to the high-frequency first portions;

a computing unit, to ascertain artifact-corrected second volume image data by applying a function, trained by way of a machine learning method, to the first volume image data; and a second interface, to output the artifact-corrected second volume image data.

A training system for adjustment of a trained function, comprising:

training interface to firstly receive a trained function, to secondly receive artifact-affected first training volume image data of a training object including a training artifact, the training artifact including high-frequency first portions in a direction of a first axis and, in a plane perpendicular to the first axis, including second portions which are low-frequency relative to the high-frequency first portions, and to thirdly receive substantially artifact-free third training volume image data of the training object; and training computing unit, to ascertain artifact-corrected third training volume image data by applying the trained function to the first training volume image data, and to adjust the trained function based upon a comparison of the second training volume image data and the third training volume image data.

A non-transitory computer program product storing a computer program, directly loadable into a memory of at least one of a correction system and a training system, including program sections to carry out the method for artifact correction of an embodiment, when the program sections are executed by the correction system the training system.

A non-transitory computer-readable storage medium, storing program sections readable and executable by at least one of a correction system and a training system, to carry out the method for the artifact correction of an embodiment, when the program sections are executed by the at least one of the correction system and the training system.

BRIEF DESCRIPTION OF DRAWINGS

The invention is explained below on the basis of example embodiments with reference to the accompanying figures. The illustrations in the figures are schematic, greatly simplified and not necessarily to scale. In the figures:

FIG. 5 shows a computed tomography device.

DETAILED DESCRIPTION OF THE EXAMPLE EMBODIMENTS

Figure 1:
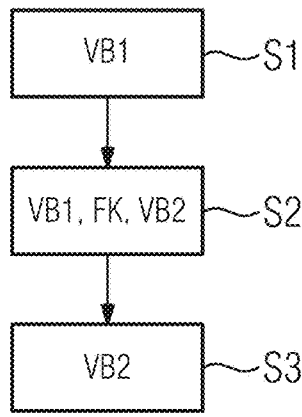
FIG. 1 shows an example embodiment of a method for artifact correction.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for the artifact correction of three-dimensional volume image data of an object, comprising the steps of receiving, ascertaining and outputting. In this context, in the step of receiving, first volume image data is received via a first interface, wherein the first volume image data is based on projection measurement data acquired via a computed tomography device, wherein the computed tomography device has a system axis, and wherein the first volume image data has an artifact which has high-frequency first portions in the direction of the system axis and, in a plane perpendicular to the system axis, has second portions which are low-frequency in relation to the high-frequency first portions. In the step of ascertaining, artifact-corrected second volume image data is ascertained by applying a trained function to the first volume image data via a computing unit.

In the step of outputting, the artifact-corrected second volume image data is output via a second interface.

The first volume image data is based on projection measurement data in particular. For example, the first volume image data is reconstructed via a filtered back projection method on the basis of the projection measurement data.

The volume image data is in particular image data which is embodied in a spatially three-dimensional manner. The volume image data has a dimension along a first axis, which in the case of volume image data measured via a computed tomography device extends in a direction along the system axis of the computed tomography device used for the acquisition of the projection measurement data. The image dimension in the direction of the first axis can accordingly be referred to as image dimension in the direction of the system axis. In general, it can also be referred to as the z axis. The second and third axes of the three-dimensional image space of the volume image data then extend perpendicular to the system axis.

In connection with the artifact mentioned above, high-frequency portions can in particular mean that the artifact has a strong variation, i.e. a strongly varying bright-dark contrast, in the direction of the system axis. In relation to this, the lower-frequency signature of the artifact in the image plane perpendicular to the first axis may be described as constant over image pixel groups. In particular, the signature of the artifact in this image plane is constant over a larger number of image pixels than the signature of the artifact in the direction of the system axis.

A trained function maps input data to output data. In this context, the output data could in particular depend upon one or more parameters of the trained function. The one or the plurality of parameters of the trained function may be determined and/or adapted by training. The determination and/or adjustment of the one or more parameters of the trained function may in particular be based on a pair of training input data and associated training mapping data, wherein the trained function is applied to the training input data in order to generate training output data. In particular, the determination and/or adjustment may be based on a comparison of the training mapping data and the training output data. In general, a trainable function, i.e. a function with one or more parameters which have not yet been adjusted, is also referred to as a trained function. Other terms for trained function are trained mapping rule, mapping rule with trained parameters, function with trained parameters, algorithm based on artificial intelligence, machine learning algorithm. One example for a trained function is an artificial neural network, wherein the edge weights of the artificial neural network correspond to the parameters of the trained function. Instead of the term "neural network", the term "neural net" can also be used. In particular, a trained function may also be a deep artificial neural network ("deep neural network"). A further example of a trained function is a "support vector machine", with other machine learning algorithms furthermore also being able to be used in particular as a trained function.

The trained function may in particular be a function which maps three-dimensional image data, i.e. volume image data, to three-dimensional image data. In particular, the second volume image data is determined on the basis of the first volume image data and on the basis of the trained function via the computing unit, when the trained function is applied to input data and, in doing so, generates output data, wherein the input data is based on the first volume image data and wherein the output data corresponds to the second volume image data. The trained function can in particular be trained to identify the artifact in the first volume image data and to generate artifact-corrected second volume image data.

The inventors have discovered that it is possible to provide high-quality and artifact-corrected volume image data by way of the method according to the invention with little, in particular without additional structural hardware outlay and/or with an improved filter performance and level of certainty in comparison with the prior art. In this manner, it is likewise possible to avoid a reduced resolution of the image data. This can in particular allow an improved diagnosis on the basis of the image data.

In one method variant, the projection measurement data in particular has a sub-sampling in the direction of the system axis.

In this context, the sub-sampling corresponds in particular to the non-fulfillment of the Shannon sampling theorem along the system axis. The sub-sampling can result, in particular as part of a multi-slice spiral CT, from the sub-sampling along the system axis which is intrinsically inherent with the X-ray detector. In particular, the artifact may be a windmill artifact. The trained function may then be trained to the identification and correction of windmill artifacts.

In accordance with a further embodiment variant, the artifact is a cone beam artifact.

In this embodiment variant, the projection measurement data is based in particular on acquisitions of the object via a multi-slice CT device, wherein the multi-slice X-ray detector is illuminated via an X-ray cone beam.

Advantageously, cone beam artifacts can be reduced by way of the method according to the invention in a time-efficient manner and with a high level of certainty.

In accordance with an advantageous embodiment of the method, the trained function is based on a neural network.

In particular, a trained function may be based on a neural network in that the trained function is identical to the neural network or that the trained function comprises the neural network. The neural network may in particular have a convolutional layer and/or a deconvolutional layer. In particular, a neural network may comprise a pooling layer. In particular, the first neural network and/or the second neural network may comprise a pooling layer. In particular, a neural network may be a convolutional neural network. In particular, a neural network may be a deep convolutional network ("deep convolutional neural network"). By using convolutional layers and/or deconvolutional layers, a neural network can be used particularly efficiently for image processing.

The inventors have discovered that a neural network can be used particularly well for image processing. As a result, a neural network advantageously enables an effective implementation of the method according to the invention with a particularly efficient correction performance.

In accordance with an advantageous method variant, the trained function is based on artifact-affected first training volume image data of a training object and on substantially artifact-free second training volume image data of the training object, wherein the first artifact-affected training volume image data has a training artifact, which has high-frequency first portions in the direction of a first axis and, in a plane perpendicular to the first axis, has second portions which are low-frequency in relation to the high-frequency first portions. The training artifact may for example correspond to a windmill artifact or a cone beam artifact.

In this context, substantially artifact-free may in particular be understood to mean that an artifact-free image impression occurs when viewing the second training volume image data. This means that an impairment of the second training volume image data by an artifact is preferably not visible. At least, however, the second training volume image data is only impaired by an artifact to a very low amount and is not hindering, in particular for a potential diagnosis on the basis of such volume image data.

In particular, the determination and/or adjustment of the one or more parameters of the trained function may be based on a pair of first training volume image data and associated second training volume image data, wherein the trained function is applied to the first training volume image data in order to generate third training volume image data. In particular, the determination and/or adjustment may be based on a comparison of the second training volume image data and the third training volume image data.

Preferably, in this context the first training volume image data or second training volume image data comprise simulated training volume image data or measured training volume image data. The training volume image data may also equally be measured or simulated training volume image data.

In particular, simulated training volume image data can be generated via known software modules, which emulate the irradiation of an object with X-ray radiation on the basis of the laws of physics and simulate the absorption and scattering of X-ray radiation by the object. In particular, this makes it possible in a simple manner to generate both artifact-free and artifact-affected computed tomography image data sets. In particular, it is also possible for an artifact to be imprinted onto existing clinical data by way of simulation, so that artifact-affected training volume image data can be formed.

The inventors have discovered that simulated training volume image data advantageously makes it possible to dispense with additional measurements of a training object and the time requirement associated therewith. Regardless of additional measurements, it is possible for a large number of training volume image data items to be provided in a particularly simple manner. In particular, a provision of artifact-free training volume image data can be enabled in a particularly favorable manner, as simulations are not restricted by physical acquisition conditions.

Measured training volume image data advantageously enables the provision of a trained function, which is based on real, measured image events. Thus, a particularly advantageous correction performance can be achieved by real, measured volume image data, where appropriate. The measured training volume image data can in particular be generated via a training computed tomography device. If the first training volume image data is based on projection measurement data acquired via a training CT device, then the first axis in particular extends according to the system axis of the training CT device.

In accordance with a preferred variant of the method, the first and/or second training volume image data comprise at least one of the following types of image data:

Image data which is based on training projection measurement data acquired via a training computed tomography device, wherein the training computed tomography device has a spring focus in the direction of a training system axis of the training computed tomography device, Image data which is based on combined training projection measurement data acquired via a training computed tomography device, wherein the training projection measurement data is combined in the direction of a training system axis of the training computed tomography device, Image data reconstructed by way of an iterative reconstruction algorithm.

If the first and/or second training volume image data is based on projection measurement data acquired via a spring focus CT device, wherein the spring focus is provided in the direction of the system axis, then substantially artifact-free second training volume image data can be provided by the volume image data being reconstructed on the basis of the projection measurement data with spring focus. Associated artifact-affected first volume image data can be provided by volume image data being reconstructed on the basis of the projection measurement data without spring focus.

If the training volume image data is based on combined projection measurement data, then the combination of the training projection measurement data may in particular be based on a combination of projection measurement data from adjacent detector rows in the direction of the system axis. The projection measurement data may be combined for the reconstruction without the projection measurement data overlapping between the detector rows, in order to generate first artifact-affected training volume image data. The measurement data may be combined for the reconstruction with an overlap between the detector rows. In particular, this means that a fulfillment of the Shannon sampling theorem can be achieved and substantially artifact-free second training volume image data can be provided.

In particular, substantially artifact-free second training volume image data can be generated by way of an iterative reconstruction method. The reconstruction can be carried out on the basis of training projection measurement data, which has a sub-sampling in the direction of the first axis. Associated artifact-affected first training volume image data may then be generated for example by way of a simpler back projection method on the basis of the same training projection measurement data.

Advantageously, image data of a training object can be provided, which has no artifact or only a very low influence of the artifact. This may be used as what is known as a "ground truth" and correspond to the training mapping data, which can be compared as part of the training or adjustment of the trained function with the output data of the trained function. Likewise, associated artifact-affected image data of the training object can be generated, which as part of the training of the trained function may serve as training input data associated with the training mapping data.

At least one embodiment of the invention additionally relates to a method for the adjustment of a trained function comprising the steps of the first receiving, the second receiving and the ascertaining, as well as the third receiving and the adjusting. In this context, in the step of the first receiving, the trained function is received via a training interface. In the step of the second receiving via the training interface, artifact-affected first volume image data of a training object is received. Here, the first training volume image data has a training artifact, wherein the training artifact has high-frequency first portions in the direction of a first axis and, in a plane perpendicular to the first axis, has second portions which are low-frequency in relation to the high-frequency first portions. In the step of the third receiving, substantially artifact-free second training volume image data of the training object is received via the training interface, wherein the second training volume image data is brought into association with the first training volume image data. In the step of ascertaining, artifact-corrected third training volume image data is ascertained by applying the trained function to the first training volume image data via a training computing unit. In the step of adjusting, the trained function is adjusted on the basis of a comparison of the second training volume image data and the third training volume image data via a training computing unit.

The first or second training volume image data may comprise training volume image data as has already been described above. In the case of training volume image data measured via a training CT device, the first axis may proceed according to the system axis of the training computed tomography device. In other words, the first axis may correspond with the training system axis.

At least one embodiment of the invention furthermore relates to a correction system for the artifact correction of three-dimensional volume image data of an object comprising a first interface embodied for receiving first three-dimensional volume image data, wherein the first volume image data is based on projection measurement data acquired via a computed tomography device, wherein the computed tomography device has a system axis, and wherein the first volume image data has an artifact which has high-frequency first portions in the direction of the system axis and, in a plane perpendicular to the system axis, has second portions which are low-frequency in relation to the high-frequency first portions. The correction system additionally comprises a computing unit, embodied for ascertaining artifact-corrected second volume image data by applying a function trained via a machine learning method to the first volume image data. Furthermore, the correction system comprises a second interface embodied for outputting the artifact-corrected second volume image data.

Such a correction system may be embodied, in particular, to carry out the method according to at least one embodiment of the invention described above and its aspects. The correction system may be embodied to carry out this method and its aspects in that the interfaces and the computing unit are embodied to carry out the corresponding method steps.

At least one embodiment of the invention additionally relates to a computed tomography device, which is embodied to acquire projection measurement data of an object and which additionally comprises a correction system according to an embodiment of the invention as has been described above.

Moreover, at least one embodiment of the invention relates to a training system for the adjustment of a trained function comprising a training interface embodied for the first receiving of the trained function, furthermore embodied for the second receiving of artifact-affected first training volume image data of a training object having a training artifact, wherein the training artifact has high-frequency first portions in the direction of a first axis and, in a plane perpendicular to the first axis, has second portions which are low-frequency in relation to the high-frequency first portions, furthermore embodied for the third receiving of substantially artifact-free third training volume image data of the training object. The training system additionally has a training computing unit, embodied for ascertaining artifact-corrected second training volume image data by applying the trained function to the first training volume image data, and furthermore embodied for adjusting the trained function on the basis of a comparison of the second training volume image data and the third training volume image data.

Such a training system may be embodied, in particular, to carry out the method according to the invention described above for adjusting a trained function, and its aspects. The training system is embodied to carry out this method and its aspects in that the interface and the computing unit are embodied to carry out the corresponding method steps.

At least one embodiment of the invention also relates to computer program products with computer programs as well as computer-readable media.

In particular, at least one embodiment of the invention relates to a computer program product with a computer program, which is able to be loaded directly into a memory of a correction system and/or of a training system, with program sections in order to carry out all steps of the method for the artifact correction of at least one embodiment and/or in order to carry out all steps of the method for the adjustment of a trained function of at least one embodiment, when the program sections are executed by the correction system and/or the training system.

In particular, at least one embodiment of the invention may relate to a computer program product having a computer program which is able to be directly loaded into a memory of a correction system, having program sections in order to carry out all steps of the method for the artifact correction of at least one embodiment when the program sections are executed by the correction system.

In particular, at least one embodiment of the invention may relate to a computer program product having a computer program which is able to be directly loaded into a memory of a training system, having program sections in order to carry out all steps of the method for the adjustment of a trained function of at least one embodiment when the program sections are executed by the training system.

In particular, at least one embodiment of the invention relates to a computer-readable storage medium, on which program sections which can be read and executed by a correction system and/or a training system are stored, in order to carry out all steps of the method for the artifact correction of at least one embodiment and/or in order to carry out all steps of the method for the adjustment of a trained function of at least one embodiment, when the program sections are executed by the correction system and/or the training system.

In particular, at least one embodiment of the invention may relate to a computer-readable storage medium on which program sections which can be read and executed by a correction system are stored, in order to carry out all steps of the method for the artifact correction of at least one embodiment when the program sections are executed by the correction system.

In particular, at least one embodiment of the invention relates to a computer-readable storage medium on which program sections which can be read and executed by a training system are stored, in order to carry out all steps of the method for the adjustment of a trained function of at least one embodiment when the program sections are executed by the training system.

A realization largely through software has the advantage that correction systems and/or training systems which are already in use can also easily be upgraded by a software update in order to operate in the manner according to at least one embodiment of the invention. Such a computer program product can comprise, where relevant, in addition to the computer program, further constituents, such as, for example, documentation and/or additional components, as well as hardware components, for example, hardware keys (dongles, etc.) in order to use the software.

FIG. 1 shows an example embodiment of a method S for artifact correction. In step S1, first volume image data VB1 is received via a first interface ST1. In this context, the first volume image data VB1 is based on projection measurement data PM acquired via a computed tomography device 1, wherein the computed tomography device 1 has a system axis AR, and wherein the first volume image data VB1 has an artifact which has high-frequency first portions in the direction of the system axis AR and, in a plane perpendicular to the system axis AR, has second portions which are low-frequency in relation to the high-frequency first portions. The volume image data is in particular spatially three-dimensional, wherein a spatial axis runs along the system axis AR of the computed tomography device 1.

The artifact may in particular be caused by the fact that the projection measurement data PM has a sub-sampling in the direction of the system axis AR. For example, the artifact is a windmill artifact. It may, however, also be a cone beam artifact.

In step S2, artifact-corrected second volume image data VB2 is ascertained by applying a trained function FK to the first volume image data VB1 via a computing unit RH. The trained function FK maps the first volume image data VB1 to the artifact-corrected second volume image data VB2, wherein the second volume image data VB2 depends upon one or more parameters of the trained function FK.

In this example embodiment, the trained function FK comprises at least one convolutional layer and one pooling layer. In particular, the trained function FK comprises a convolutional neural network (CNN for short), wherein the first volume image data VB1 is used as an input value for the convolutional neural network. In particular, the trained function FK may be a fully convolutional neural network (FCNN for short), wherein an FCNN is a CNN, wherein the last completely connected layer of the CNN is replaced by a convolutional layer and/or deconvolutional layer. The trained function FK may also be embodied as a convolutional neural network in the sense of a U-net, for example. The trained function FK may also be embodied as an artificial neural network in the sense of an autoencoder.

It is conceivable that the trained function FK, in one example embodiment, comprises a three-dimensional volume filter having a plurality of filter parameters, wherein the filter parameters of the volume filter are merely trained for the identification and correction of the artifact or are adjusted in a method according to an embodiment of the invention for the adjustment of a trained function FK. An implementation of a volume filter of this kind could feature an isolation of the artifacts by a high-pass filtering in the z direction (along the system axis) and a low-pass or band-pass filtering in a plane perpendicular thereto. Subsequently, in a subtraction step, the artifacts isolated via the volume filter may be removed from the original data, i.e. the first volume image data.

In the example embodiment shown, the trained function FK is in particular based on first training volume image data TVB1 and associated second training volume image data TVB2 of a training object, wherein the first training volume image data TVB1 comprises artifact-affected training volume image data and the second training volume image data TVB2 comprises substantially artifact-free training volume image data. In particular, the first training volume image data TVB1 has a training artifact, which has high-frequency first portions in the direction of a first axis and, in a plane perpendicular to the first axis, has second portions which are low-frequency in relation to the high-frequency first portions. The training artifact may for example be a windmill artifact or a cone beam artifact. In particular, the one or more parameters of the trained function FK are based on a pair consisting of first training volume image data TVB1 and associated second volume image data TVB2. In particular, the one or more parameters of the trained function FK may be determined or adjusted on the basis of a pair consisting of first artifact-affected training volume image data TVB1 and associated second substantially artifact-free volume image data TVB2.

The first and/or second training volume image data TVB1, TVB2 may comprise measured and/or simulated training volume image data. The first and/or second training volume image data TVB1, TVB2 may for example comprise image data which is based on training projection measurement data acquired via a training computed tomography device, wherein the training computed tomography device has a spring focus in the direction of the system axis. The first and/or second training volume image data TVB1, TVB2 may for example comprise image data which is based on combined training projection measurement data acquired via a training computed tomography device, wherein the training computed tomography device has a training system axis and wherein the training projection measurement data is combined in the direction of the training system axis. The first and/or second training volume image data TVB1, TVB2 may for example comprise image data which is reconstructed by way of an iterative reconstruction algorithm.

In step S3, the artifact-corrected second volume image data VB2 is output via a second interface ST2. For example, the second volume image data VB2 may be output to a further image processing stage.

For example, the second volume image data VB2 may be output to a display unit DE.

Figure 2:
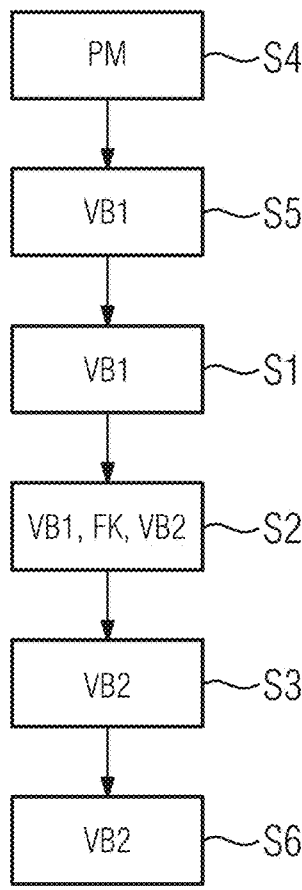
FIG. 2 shows a further example embodiment of a method for artifact correction.

FIG. 2 shows a further example embodiment of the method S for artifact correction. The example embodiment additionally has the step S4 of acquiring projection measurement data PM via a computed tomography device 1, the step S5 of reconstructing first three-dimensional volume image data VB1 via a reconstruction unit RK and the step S6 of displaying the substantially artifact-free second volume image data VB2 via a display unit DE.

The projection measurement data is in particular acquired via a multi-slice spiral computed tomography device 1 or a multi-slice computed tomography device 1. The reconstruction unit RK is in particular embodied to reconstruct three-dimensional volume image data on the basis of the projection measurement data PM, for example by way of a filtered back projection method. Via the first interface ST1, the reconstructed volume image data is subsequently received for the application of the method according to an embodiment of the invention.

Figure 3:
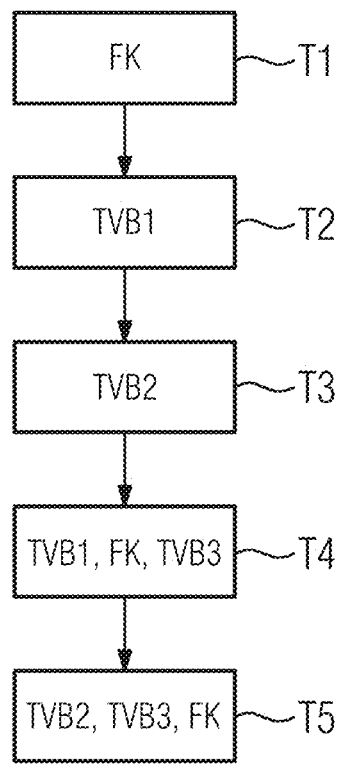
FIG. 3 shows an example embodiment of a method for the adjustment of a trained function.

FIG. 3 shows a method T for the adjustment of a trained function FK. In the step T1 of the first receiving, the trained function FK is received via a training interface TST1. In the step T2 of the second receiving, artifact-affected first training volume image data TVB1 of a training object is received via the training interface TST. Here, the first training volume image data TVB1 has a training artifact, wherein the training artifact has high-frequency first portions in the direction of a first axis and, in a plane perpendicular to the first axis, has second portions which are low-frequency in relation to the high-frequency first portions. In the step T3 of the third receiving, substantially artifact-free second training volume image data TVB2 of the training object is received via the training interface TST, wherein the second training volume image data TVB2 is brought into association with the first training volume image data TVB1. The second training volume image data TVB2 may also be referred to as being associated with the first training volume image data TVB1 and vice versa. In the step T4 of ascertaining, artifact-corrected third training volume image data TVB3 is ascertained by applying the trained function FK to the first training volume image data TVB1 via a training computing unit TRH. In the step T5 of adjusting, the trained function FK is adjusted on the basis of a comparison of the second training volume image data TVB2 and the third training volume image data TVB3 via a training computing unit TRH.

The first and second training volume image data may comprise training volume image data as has been described above.

The comparison of the second training volume image data TVB2 and the third training volume image data TVB3 in the step of adjusting T5 may for example be based on the pixel-based difference between the second three-dimensional training volume image data TVB2 and the third three-dimensional training volume image data TVB3, for example on the sum of squared deviation. In this context, one or more parameters of the trained function FK may then be adjusted such that the sum of squared deviation is minimized.

In this example embodiment, the trained function FK is already pre-trained, i.e. one or more parameters of the trained function FK have been adjusted by the described training method and/or by another training method.

Alternatively, the one or more parameters of the trained function FK may not yet be adjusted via training data, in particular the one or more parameters may be preallocated with a constant value and/or with a random value. In particular, all parameters of the trained function FK may not yet be adjusted via training data, in particular all parameters may be preallocated with a constant value and/or with a random value.

Figure 4:
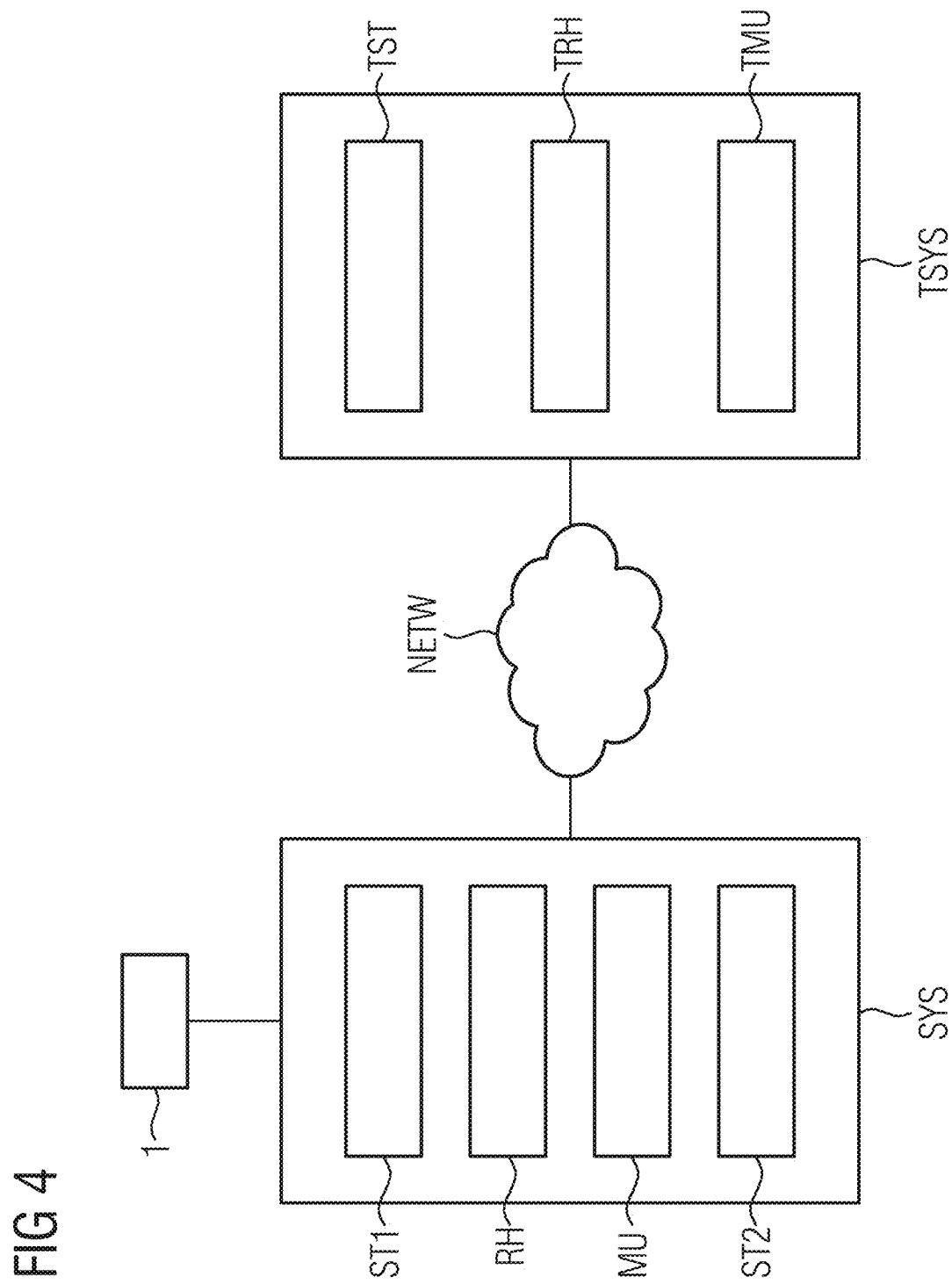
FIG. 4 shows an example embodiment of a correction system and a training system.

FIG. 4 shows a correction system SYS for the artifact correction of three-dimensional volume image data as well as a training system TSYS for the training or adjustment of a trained function FK. The correction system SYS shown here and the training system TSYS shown here are embodied to carry out one or more of the methods according to an embodiment of the invention. The correction system SYS comprises a first interface ST1, a computing unit RH, a second interface ST2 as well as a memory unit MU. The training system TSYS comprises a training interface TST, a training computing unit TRH as well as training memory unit TMU.

The correction system SYS and/or the training system TSYS may in particular involve a computer, a microcontroller or an integrated circuit. Alternatively, the correction system SYS and/or the training system TSYS may involve a real or virtual network of computers (a specialist term for a real network is "cluster", while a specialist term for a virtual network is "cloud").

An interface ST1, ST2 or training interface TST may involve a hardware or software interface (for example, PCI bus, USB or Firewire). A computing unit RH or training computing unit TRH may have hardware elements or software elements, for example, a microprocessor or what is known as an FPGA (Field Programmable Gate Array).

A memory unit MU or training memory unit TMU may be realized as a non-permanent working memory (Random Access Memory, RAM for short) or as a permanent mass storage unit (hard disk, USB stick, SD card, solid state disk). Optimally, the correction system SYS and/or the training system TSYS may furthermore comprise an input and output unit, wherein an input and output unit comprises at least one input unit and/or at least one output unit.

In the example embodiment shown, the correction system SYS is connected to the training system TSYS via a network NETW, furthermore the correction system SYS is directly connected to a computed tomography device 1. The connection to the computed tomography device 1 may also, however, be established via the network NETW. The correction system SYS may also, however, be part of a computed tomography device 1. Furthermore, the communication between the correction system SYS and the training system TSYS may also take place offline, for example by way of an exchange of data carriers.

Communication between the correction system SYS and the training system TSYS may, for example, consist in the correction system SYS transmitting further training data to the training system TSYS, or the training system TSYS transmitting the trained function to the correction system SYS. Furthermore, the training system TSYS may further be connected to other data sources, in particular to a local or distributed PACS (Picture Archiving and Communication System).

The correction system SYS shown here is embodied to carry out the example embodiments of the method S for the artifact correction of three-dimensional volume image data of an object (13), in that the first and the second interface ST1, ST2 and the computing unit RH are embodied to carry out the respective steps of the method. The training system TSYS shown here is embodied to carry out the example embodiments of the method T for the training or adjustment of a trained function FK, in that the interface TST and the computing unit TRH are embodied to carry out the respective steps of the method.

The network NETW may involve a local network (Local Area Network, LAN for short) or a large-scale network (Wide Area Network, WAN for short). An example of a local network is an intranet; an example of a wide area network is the Internet. The network NETW may in particular be also designed as wireless, in particular as a WLAN (Wireless LAN; the abbreviation "Wi-Fi" is common) or as a Bluetooth connection. The network NETW may also be designed as a combination of the cited examples.

FIG. 5 shows a computed tomography device 1 with an X-ray tube 26. The computed tomography device 1 has a gantry 20, a tunnel-shaped opening 9 and a positioning apparatus 10. The gantry 20 features the support frame 21 and the rotating assembly 24. The rotating assembly 24 is arranged on the support frame 21 such that it is able to rotate about an axis of rotation AR relative to the support frame 21 via a rotating positioning apparatus.

The object 13, in this case a patient 13, is able to be introduced into the tunnel-shaped opening 9. In the tunnel-shaped opening 9, a region of the object 13 to be mapped is able to be positioned such that the X-ray radiation 27 can pass from the X-ray tube 26 to the region to be mapped and, after interacting with the region to be mapped, can reach the X-ray detector 28. The positioning apparatus 10 features the positioning base 11 and the positioning table 12 for positioning the object 13. The positioning table 12 is arranged on the positioning base 11 so as to be able to move in relation to the positioning base 11, such that the positioning table 12 is able to be introduced into the tunnel-shaped opening 9 in a longitudinal direction of the positioning table 12, in particular substantially along the system axis AR.

The computed tomography device 1 is embodied to acquire projection measurement data on the basis of X-ray radiation 27.

The X-ray tube 26 is arranged on the rotating assembly 24 and is embodied to emit the X-ray radiation 27. The X-ray detector 28 is embodied to detect the X-ray radiation 27. The X-ray radiation 27 is able to pass from the X-ray tube 26 to the region of the object 13 to be mapped and, after interacting with the region to be mapped, can strike the X-ray detector 28. In this way, measurement data of the region can be captured in the form of projection measurement data.

In this example embodiment, the computed tomography device 1 in particular comprises a multi-slice X-ray detector 26, which has a plurality of detector lines or rows in the direction of the system axis AR. The computed tomography device may in particular be embodied as a spiral computed tomography device, wherein the object experiences a continuous feed through the computed tomography device, while the X-ray tube 26 and the X-ray detector 28 steadily rotate around the object.

The computed tomography device 1 additionally comprises a correction system SYS according to an embodiment of the invention, which is embodied to carry out a method S for the artifact correction of three-dimensional volume image data. In the example embodiment shown, the correction system SYS has a reconstruction unit RK. The reconstruction unit RK is embodied to generate three-dimensional volume image data on the basis of projection measurement data. The generated volume image data may in particular be artifact-affected first volume image data. Alternatively, it is also possible for the reconstruction unit to be embodied separately from the correction system. The memory unit MU may in particular be embodied to store the first or the second volume image data. The memory unit may additionally be embodied to store the trained function. The computed tomography device 1 additionally has a display unit DE. The second volume image data may in particular be output to the display unit DE via the second interface ST2. The display unit DE is in particular embodied to display the second volume image data or show it to a user. The display unit may have a display, for example a monitor, for this purpose.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35

U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for artifact correction of three-dimensional volume image data of an object, comprising:
receiving first volume image data via a first interface, the first volume image data being based on projection measurement data acquired via a computed tomography device, the first volume image data including an artifact, the artifact including high-frequency first portions in a direction of a first system axis of the computed tomography device, the artifact including second portions in a plane perpendicular to the first system axis, and the second portions being lower frequency than the first portions;
ascertaining, via a computing unit, artifact-corrected second volume image data by applying a trained function to the first volume image data, the trained function being based on first artifact-affected training volume image data of a training object and second substantially artifact-free training volume image data of the training object, the first artifact-affected training volume image data including a training artifact, the training artifact having high-frequency third portions in a direction of a first axis and fourth portions in a plane perpendicular to the first axis, and the fourth portions being lower frequency than the third portions; and
outputting the artifact-corrected second volume image data via a second interface.

2. The method of claim 1, wherein the projection measurement data is based on a sub-sampling in the direction of the first system axis.

3. The method of claim 2, wherein the artifact is a windmill artifact.

4. The method of claim 2, wherein the trained function is based on a neural network.

5. The method of claim 2, wherein the first artifact-affected training volume image data or the second substantially artifact-free training volume image data includes:
simulated training volume image data; or
measured training volume image data.

6. The method of claim 1, wherein the artifact is a windmill artifact.

7. The method of claim 1, wherein the artifact is a cone beam artifact.

8. The method of claim 1, wherein the trained function is based on a neural network.

9. The method of claim 1, wherein the first artifact-affected training volume image data or the second substantially artifact-free training volume image data includes:
simulated training volume image data; or
measured training volume image data.

10. The method of claim 9, wherein the first artifact-affected training volume image data or the second substantially artifact-free training volume image data includes at least one of:
first image data based on first training projection measurement data acquired via a first training computed tomography device, the first training computed tomography device including a spring focus in a direction of a first training system axis of the first training computing tomography apparatus;
second image data based on second training projection measurement data acquired via a second training computed tomography device, the second training projection measurement data being combined in a direction of a second training system axis of the second training computed tomography device; or
third image data reconstructed by way of an iterative reconstruction algorithm.

11. The method of claim 1, wherein the first artifact-affected training volume image data or the second substantially artifact-free training volume image data includes at least one of:
first image data based on first training projection measurement data acquired via a first training computed tomography device, the first training computed tomography device including a spring focus in a direction of a first training system axis of the first training computed tomography device;
second image data based on second training projection measurement data acquired via a second training computed tomography device, the second training projection measurement data being combined in a direction of a second training system axis of the second training computed tomography device; or
third image data reconstructed by way of an iterative reconstruction algorithm.

12. A non-transitory computer readable medium storing a computer program, directly loadable into a memory of a system, including program sections to carry out the method for artifact correction of claim 1, when the program sections are executed by at least one processor of the system.

13. A non-transitory computer-readable storage medium, storing program sections readable and executable by at least one of a correction system or a training system, to carry out the method for the artifact correction of claim 1, when the program sections are executed by the at least one of the correction system or the training system.

14. A correction system for artifact correction of three-dimensional volume image data of an object, comprising:
a first interface to receive first three-dimensional volume image data, the first three-dimensional volume image data being based on projection measurement data acquired via a computed tomography device, the three-dimensional first volume image data including an artifact, the artifact including high-frequency first portions in a direction of a system axis of the computed tomography device, the artifact including second portions in a plane perpendicular to the system axis, and the second portions being lower frequency than the first portions;
processing circuitry to ascertain artifact-corrected second volume image data by applying a function to the first three-dimensional volume image data, the function being trained by way of a machine learning method based on first artifact-affected training volume image data of a training object and second substantially artifact-free training volume image data of the training object, the first artifact-affected training volume image data including a training artifact, the training artifact having high-frequency third portions in a direction of a first axis and fourth portions in a plane perpendicular to the first axis, and the fourth portions being lower frequency than the third portions; and
a second interface to output the artifact-corrected second volume image data.

15. The correction system of claim 14, wherein the projection measurement data is based on a sub-sampling in the direction of the system axis.

16. A computed tomography device, embodied for acquiring projection measurement data of an object, the computed tomography device comprising the correction system of claim 14.

17. The correction system of claim 14, wherein the artifact is a windmill artifact.

18. The correction system of claim 14, wherein the artifact is a cone beam artifact.

19. The correction system of claim 14, wherein the machine learning method is based on a neural network.

20. The correction system of claim 14, wherein the first artifact-affected training volume image data or the second substantially artifact-free training volume image data includes:
    simulated training volume image data; or
    measured training volume image data.

21. The correction system of claim 14, wherein the first artifact-affected training volume image data or the second substantially artifact-free training volume image data includes at least one of:
    first image data based on first training projection measurement data acquired via a first training computed tomography device, the first training computed tomography device including a spring focus in a direction of a first training system axis of the first training computed tomography device;
    second image data based on second training projection measurement data acquired via a second training computed tomography device, the second training projection measurement data being combined in a direction of a second training system axis of the second training computed tomography device; or
    third image data reconstructed by way of an iterative reconstruction algorithm.

22. The correction system of claim 20, wherein the first artifact-affected training volume image data or the second substantially artifact-free training volume image data includes at least one of:
    first image data based on first training projection measurement data acquired via a first training computed tomography device, the first training computed tomography device including a spring focus in a direction of a first training system axis of the first training computed tomography device;
    second image data based on second training projection measurement data acquired via a second training computed tomography device, the second training projection measurement data being combined in a direction of a second training system axis of the second training computed tomography device; or
    third image data reconstructed by way of an iterative reconstruction algorithm.

* * * * *